United States Patent
Tanigawa

(10) Patent No.: US 7,608,044 B2
(45) Date of Patent: Oct. 27, 2009

(54) ULTRASONIC IMAGE DISPLAY METHOD AND ULTRASONIC DIAGNOSIS APPARATUS

(75) Inventor: Shunichiro Tanigawa, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 370 days.

(21) Appl. No.: 11/200,813

(22) Filed: Aug. 10, 2005

(65) Prior Publication Data

US 2006/0058666 A1 Mar. 16, 2006

(30) Foreign Application Priority Data

Aug. 18, 2004 (JP) .............................. 2004-237926

(51) Int. Cl.
*A61B 8/14* (2006.01)
(52) U.S. Cl. .................. 600/441; 600/437; 600/438; 600/439; 600/443; 600/447; 600/449; 600/450; 600/458; 600/459
(58) Field of Classification Search .................. 600/437, 600/439, 440, 441, 443, 447, 449, 450, 458, 600/459, 438
See application file for complete search history.

(56) References Cited

U.S. PATENT DOCUMENTS

| 4,794,932 | A | | 1/1989 | Baba |
| 5,882,315 | A | * | 3/1999 | Ji et al. ........................ 600/553 |
| 5,931,784 | A | | 8/1999 | Kajiwara et al. |
| 6,099,471 | A | | 8/2000 | Torp et al. |
| 6,322,510 | B1 | | 11/2001 | Kataoka et al. |
| 6,517,485 | B2 | | 2/2003 | Torp et al. |
| 6,679,843 | B2 | * | 1/2004 | Ma et al. ..................... 600/441 |
| 6,884,216 | B2 | * | 4/2005 | Abe et al. ................... 600/440 |
| 2005/0085729 | A1 | | 4/2005 | Abe |

FOREIGN PATENT DOCUMENTS

WO 9734530 9/1997

* cited by examiner

*Primary Examiner*—Brian Casler
*Assistant Examiner*—Baisakhi Roy
(74) *Attorney, Agent, or Firm*—Armstrong Teasdale LLP

(57) ABSTRACT

An ultrasonic image display method for displaying a composite image made from a B mode image and a tissue velocity image of an object taken by means of ultrasound. The method includes decreasing the weight of the B mode image while increasing the weight of the tissue velocity image, in response to increase of brightness of the B mode image, adding thus weighted B mode image and tissue velocity image, and displaying an image obtained by the addition.

20 Claims, 4 Drawing Sheets

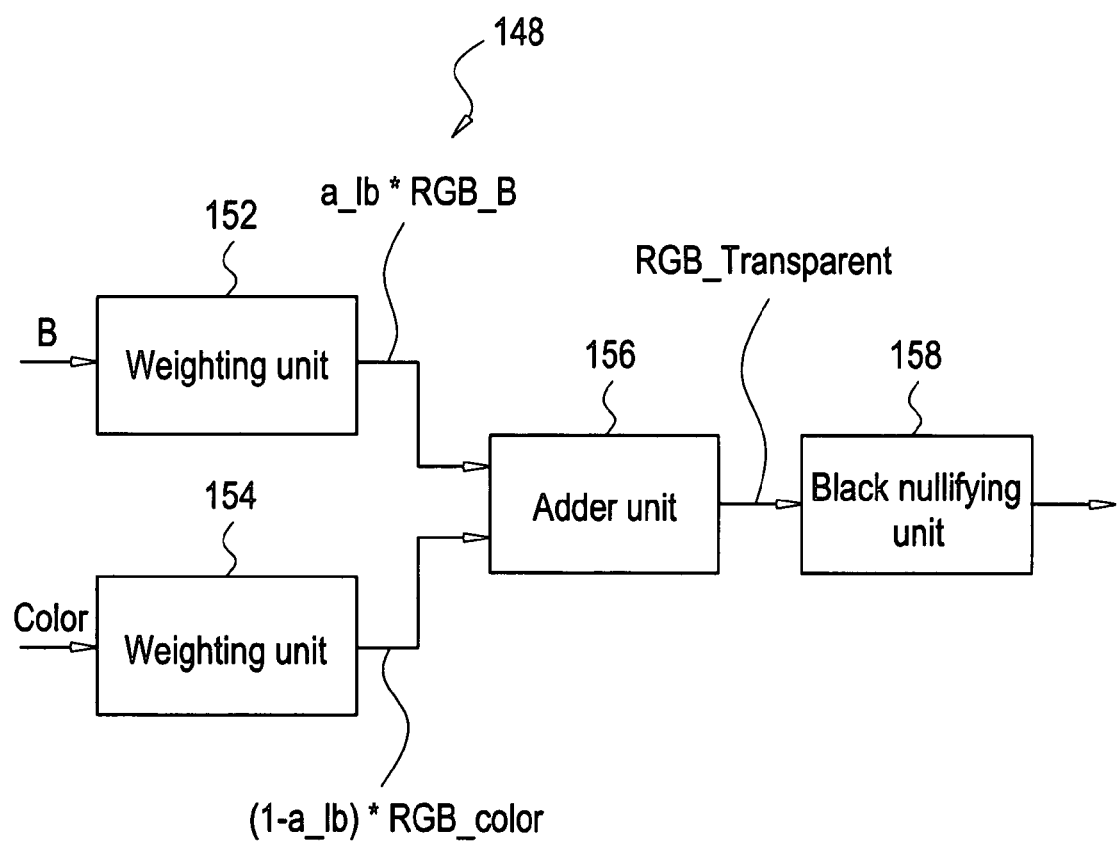

ULTRASONIC IMAGE DISPLAY METHOD AND ULTRASONIC DIAGNOSIS APPARATUS

CROSS REFERENCE TO RELATED APPLICATIONS

This application claims the benefit of Japanese Application No. 2004-237926 filed Aug. 18, 2004.

BACKGROUND OF THE INVENTION

The present invention relates to an ultrasonic image display method and an ultrasonic diagnosis apparatus. More specifically the present invention relates to an ultrasonic image display method in which the composite image is displayed from a B mode image and a tissue velocity image of an object, taken by means of ultrasound, and to an ultrasonic diagnosis apparatus, which takes the B mode image and tissue velocity image of an object by means of ultrasound to display a composite image of those two images.

The ultrasonic diagnosis apparatus takes a B mode image and tissue velocity image of an object by means of ultrasound to display a composite image of those two images. Doppler signals of ultrasonic echo are used for the echogram of tissue velocity images (for example, see Patent document 1).

Patent document 1: specification of U.S. Pat. No. 6,517,485 (columns 7 to 13, and FIGS. 3 to 4)

The composite image is a superposition of a color tissue velocity image on a monochrome B mode image. As the impression of the color tissue velocity image is stronger and the monochrome B mode image is barely seen, the composite image of such kind is not always appropriate.

SUMMARY OF THE INVENTION

Therefore, an object of the present invention is to achieve an ultrasonic image display method and ultrasonic diagnosis apparatus for displaying a composite image of B mode image and a tissue velocity image in a fashion much suitable.

In an aspect for solving the problem, the present invention provides an ultrasonic image display method for displaying a composite image made from a B mode image and a tissue velocity image of an object taken by means of ultrasound, including decreasing the weight of the B mode image while increasing the weight of the tissue velocity image, in response to increase of brightness of the B mode image; adding thus weighted B mode image and tissue velocity image; and displaying an image obtained by the addition.

In another aspect for solving the problem, the present invention provides ultrasonic diagnosis apparatus, for taking a B mode image and a tissue velocity image of an object by means of ultrasound to display a composite image of these two images, including: a weight adjustor means for decreasing the weight of B mode image in response to the increase of brightness of B mode image, while increasing the weight of tissue velocity image; an adder means for adding thus weighted B mode image and tissue velocity image; and a display means for displaying an image obtained from the addition.

It is preferable that the variation cha of the weight is a linear function of the brightness, for the purpose of appropriate adjustment of weight. It is also preferable that the linear function is a polygonal linear function for the purpose of more appropriate adjustment of weight.

In addition, it is preferable that the linear function is a concatenation of a plurality of linear functions for the purpose of much easier setting of polygonal functions. It is further preferable that the joint of the plurality of linear functions is variable, for the purpose of facilitating the modification of polygonal linear function characteristics. It is also preferable that the slope of the plurality of linear functions is variable for the purpose of facilitating the modification of the polygonal linear function characteristics.

It is preferable that for the B mode image and the tissue velocity image, the black section where the brightness of B mode image is below a predetermined threshold is nullified, for the purpose of better display of a composite image. It is furthermore preferable that the threshold is variable such that the range of nullified black image is adjustable.

In accordance with the present invention, which allow displaying a composite image of B mode image and tissue velocity image by decreasing the weight of weighted addition of B mode image in the composite image while increasing the weight of weighted addition of tissue velocity image in response to the increase of brightness of the B mode image, the composite image of B mode image and tissue velocity image can be displayed appropriately.

Further objects and advantages of the present invention will be apparent from the following description of the preferred embodiments of the invention as illustrated in the accompanying drawings.

BRIEF DESCRIPTION OF THE DRAWINGS

FIG. 4 shows a schematic block diagram illustrating the processor capability.

DETAILED DESCRIPTION OF THE INVENTION

Figure 1:
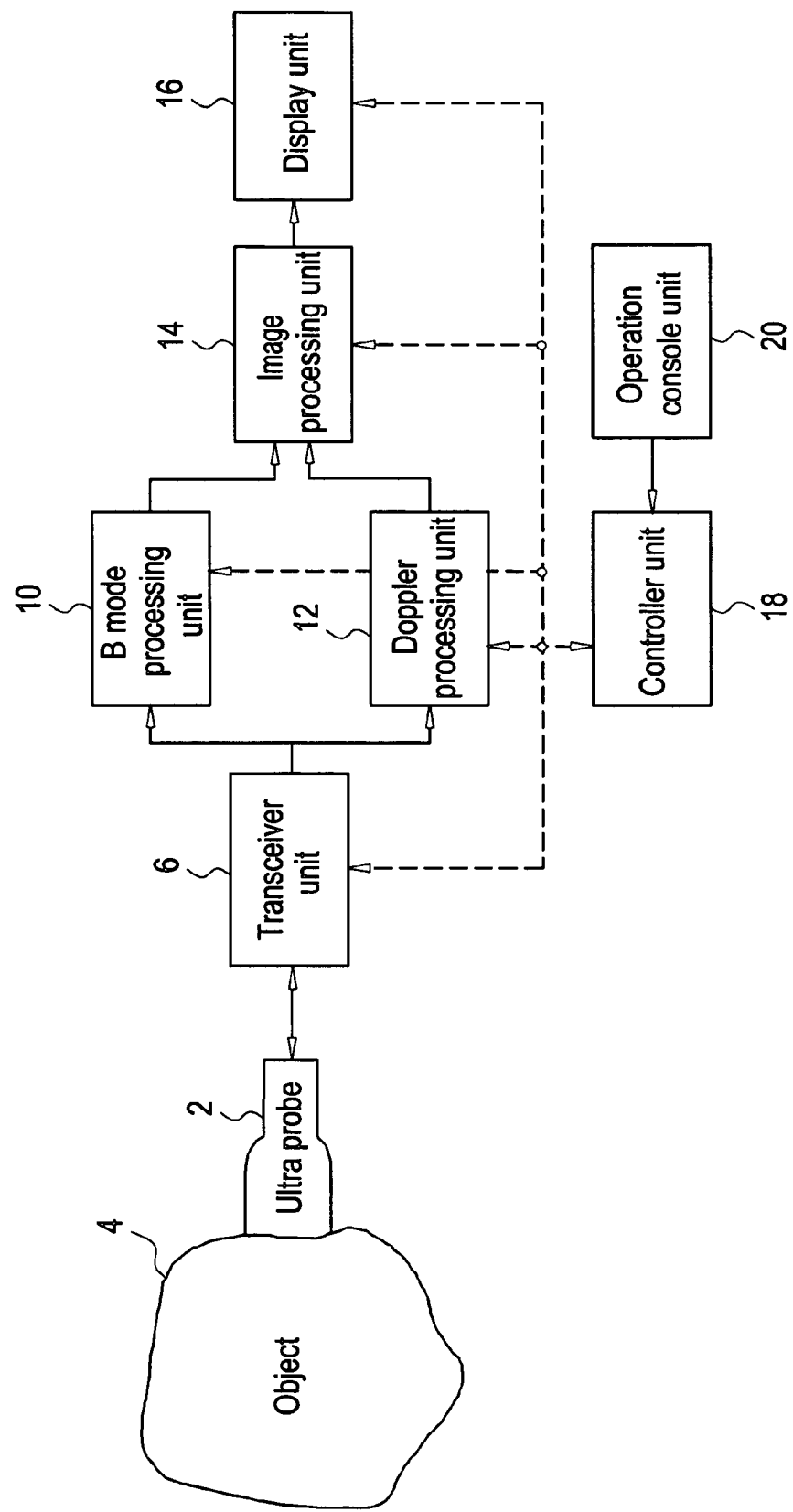
FIG. 1 shows a schematic block diagram of an ultrasonic diagnosis apparatus in accordance with one embodiment of the best mode for carrying out the invention.

Now the present invention will be described in greater details herein below with reference to the accompanying drawings. It should be noted that the description of embodiment is not to be considered to limit the present invention. FIG. 1 shows a schematic block diagram of an ultrasonic diagnosis apparatus. The apparatus is an exemplary embodiment for carrying out the invention. The structure of the apparatus illustrates an example of the best mode for carrying out the invention of ultrasonic diagnosis apparatus. The operation of the apparatus illustrates an example of the best mode for carrying out the invention of ultrasonic diagnosis apparatus.

As shown in FIG. 1, the apparatus has an ultrasonic probe 2. The ultrasonic probe 2 has an array of a plurality of ultrasound transducers not shown in the figure. Each transducer is made of a piezoelectric material, such as for example PZT ceramics (Plumb Zirconate Titanate). An operator uses the ultrasonic probe 2 by contacting the object 4.

The ultrasonic probe 2 is connected to a transceiver unit 6. The transceiver unit 6 transmits driving signals to the ultrasonic probe 2 to generate ultrasound waves. The transceiver unit 6 also receives the echo signals received by the ultrasonic probe 2.

The transmission and reception of ultrasound waves is conducted by scanning an imaging range with the ultrasonic beam, i.e., sonic line. Types of sonic line scan include the sector scan, convex scan, and linear scan.

The transceiver unit 6 is connected to a B mode processing unit 10 and to the Doppler processing unit 12. The echo receiver signals for every sonic scan line output from the transceiver unit 6 is input into the B mode processing unit 10 and the Doppler processing unit 12.

The B mode processing unit 10 generates a B mode image. The B mode processing unit 10 retrieves signals indicative of the intensity of echo at each reflection point on the sonic scan line, namely A scope signals to use the transient amplitude of A scope signals as brightness value to generate a B mode image.

The Doppler processing unit 12 generates a tissue velocity image. The Doppler processing unit 12 performs an orthogonal detection of echo receiver signals to obtain I, Q signals to process in MTI (Moving Target Indication) to obtain echo complex Doppler signals, and based on which it determines the tissue velocity image for respective sonic scan line by a predetermined operation.

Although Doppler signals includes the component of blood velocity in addition to the component of tissue velocity, only the tissue velocity component is extracted by using the difference of velocity domain of both components to thereby determine the tissue velocity image.

The B mode processing unit 10 and the Doppler processing unit 12 are connected to an image processing unit 14. The image processing unit 14 uses image data input from the B mode processing unit 10 and the Doppler processing unit 12 to generate an image for display. The B mode image is generated as monochrome image. The tissue velocity image is generated as color image. The color image represents the velocity direction as color hue.

Figure 2:
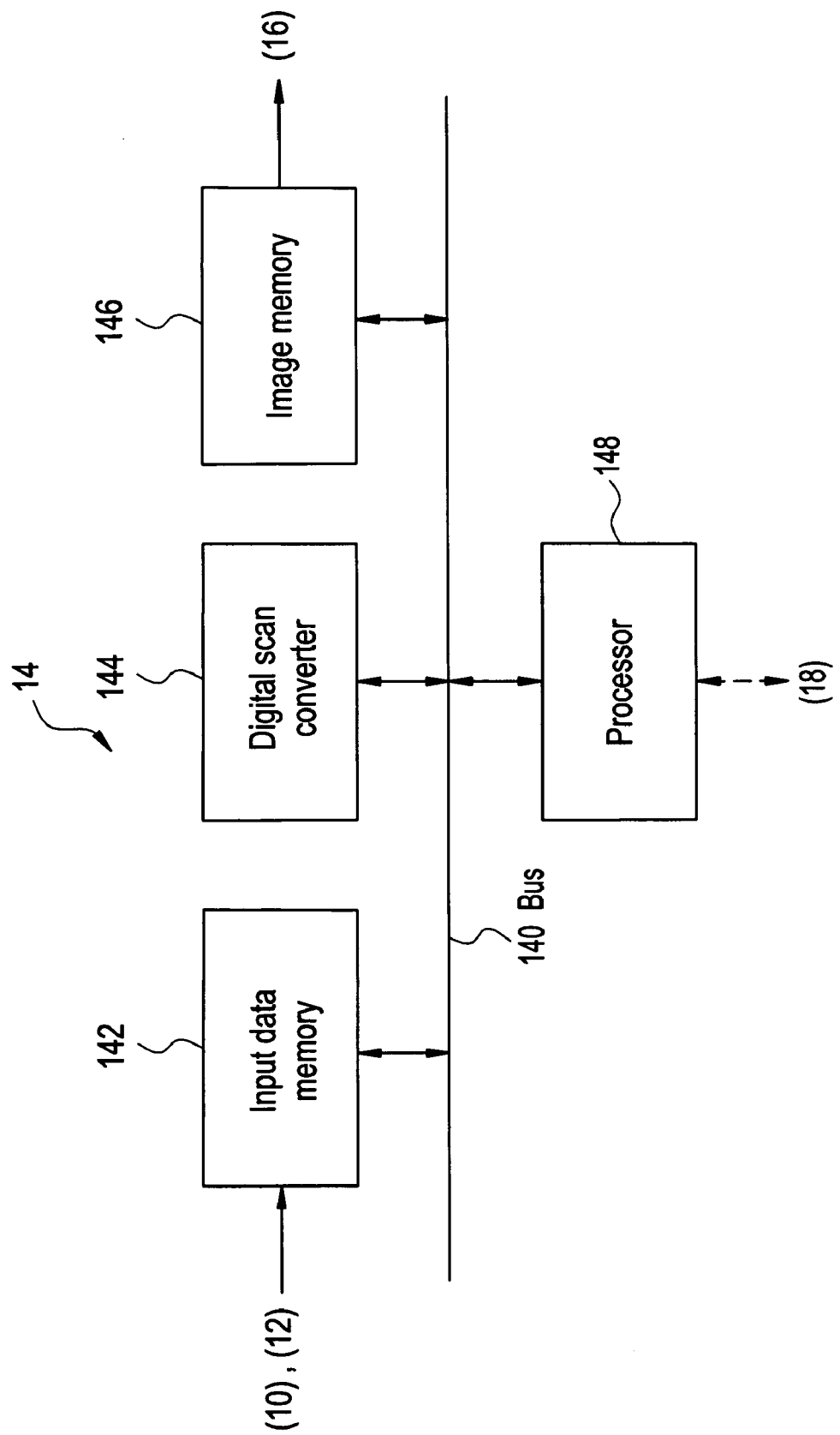
FIG. 2 shows a schematic block diagram of an image processing unit.

The image processing unit 14 includes, as shown in FIG. 2, a input data memory 142, a digital scan converter 144, an image memory 146, and a processor 148, all of which are connected through a bus 140.

The B mode image and tissue velocity image input from the B mode processing unit 10 and the Doppler processing unit 12 as sonic scan lines are stored in the input data memory 142. The data in the input data memory 142 is scan-converted by the digital scan converter 144 to store in the image memory 146. The processor 148 performs data processing for display on the data in the input data memory 142 and in the image memory 146. The data processing for display will be described later.

The image processing unit 14 is connected to a display unit 16. The display unit 16 is fed with image signals from the image processing unit 14 and based on which it displays an image. The display unit 16 is an exemplary embodiment of the display means in accordance with the present invention. The display unit 16 is constituted of for example a graphic display that can display color images.

A controller unit 18 is connected to the above-cited transceiver unit 6, B mode processing unit 10, Doppler processing unit 12, image processing unit 14 and display unit 16. The controller unit 18 supplies control signals to other units to control the operation thereof. It receives various information signals from those units under the control.

Under the control of the controller unit 18, B mode photographic operation and tissue velocity photographic operation are performed. The controller unit 18 is connected to an operation console unit 20. The operation console unit 20 is operated by an operator to input appropriate instructions and information to the controller unit 18. The operation console unit 20 may be constituted of for example an operation panel having a keyboard, a pointing device, and other operating devices.

Now the data processing for display will be described. The data processing for display is a process for generating a composite image made from a B mode image and a tissue velocity image. The composite image can be generated by weighted addition of a B mode image to a tissue velocity image.

Figure 3:
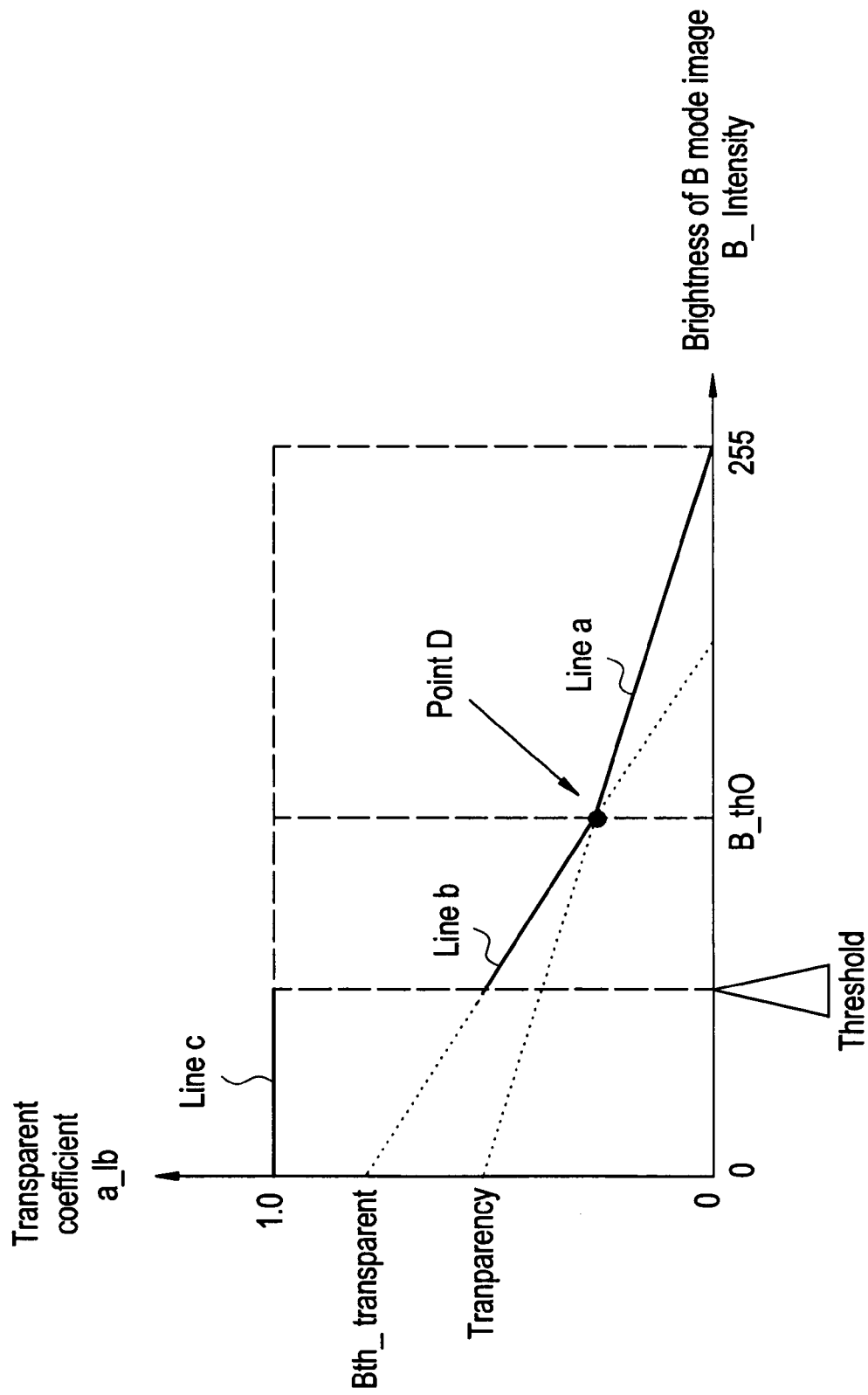
FIG. 3 shows an exemplary graph used for the weight adjustment.

FIG. 3 shows an example of graph used for weight control. The graph shown in the figure uses the brightness value of B mode image (B_Intensity) as its transverse axis and the transparency coefficient a_Ib as its vertical axis. The range of brightness values B_Intensity may be for example 0 to 255. B_Intensity=0 indicates the lowest brightness, while B_Intensity=255 indicates the highest brightness. The range of transparency coefficient a_Ib is from 0 to 1. a_Ib=0 indicates complete opaque, while a_Ib=1 indicates complete transparency.

The transparency coefficient a_Ib indicates the degree of transparency of the tissue velocity image when the composite image is made by superposing the tissue velocity image on the B mode image. This means that the tissue velocity image is completely opaque when a_Ib=0. In this case, the underlying B mode image is not visible, hidden by the tissue velocity image, so that the composite image may become the image made of solely the tissue velocity image. On the other hand, when a_Ib=1, the tissue velocity image is completely transparent. In this case, the tissue velocity image is invisible, therefore the composite image is made of solely B mode image. When 0<a_Ib<1, the tissue velocity image is translucent, corresponding to the value of a_Ib. In this case, the B mode image can be seen through the tissue velocity image.

The composite image may be thought to be formed by superposing a tissue velocity image on a B mode image. In this context when a_Ib=0 the B mode image is totally transparent, and when a_Ib=1 the B mode image is totally opaque, and when 0<a_Ib<1 the B mode image is translucent. In this situation, the composite image thus obtained is identical. In the description which follows, the composite image is considered to be formed by superposing a tissue velocity image on a B mode image, as a matter of convenience.

The line a, which constitutes part of the graph, is a linear function that crosses the transversal axis at B_Intensity=255, and vertical axis at a_Ib–Transparency, and may be given by the following equation:

$$a\_Ib = \text{transparency} \times \frac{(256 - B\_Intensity)}{256}$$

The line b, which constitutes another part of the graph, is another linear function that crosses the line a at the point D, and the vertical line at a_Ib–Bth_Transparent, and may be given by the following equation:

$$a\_Ib = \frac{\text{transparency} \times (256 - Bth\_0)/256 - Bth\_transparent}{Bth\_0} \times B\_Intensity + Bth\_transparent$$

The line c, which constitutes the rest of the graph, is a zero-order function that crosses the vertical line at a_Ib=1.

For the brightness value B_Intensity, the setting point of crossing B_th0 and the threshold value Threshold are configurable. The setting point of crossing B_th0 is a setting value for specifying the position of point D, namely the position of crossing of line a with line b. This specifies the joint between the line a and the line b. The threshold value Threshold is a setting value that specifies the end point of line c. These setting values B_th0 and Threshold can be arbitrarily set and adjusted by the operator through the operation console unit 20.

The crossing points of vertical axis with lines a and b, namely Transparency and Bth_transparent can be arbitrarily set and adjusted through the operation console unit 20. The adjustment of Transparency and Bth_transparent changes the slope of lines a and b, respectively.

Using these three lines a, b, and c, the transparency of the tissue velocity image in the composite image can be adjusted. The transparency adjustment can be performed based on the brightness value B_Intensity of each of the pixels that constitute the B mode image.

When B_Intensity<Threshold, the transparency coefficient of the tissue velocity image is determined by line c. This makes a_Ib=1, resulting in the composite image derived from solely B mode image, with the tissue velocity image being completely transparent. Along with this processing, another operation that makes B mode image with nullified black. Since the tissue velocity image that is completely transparent is nullified in black section, both images are nullified in black section, accordingly.

As noted above, in the range where B_Intensity<Threshold, the B mode image and tissue velocity image are nullified in black section to prevent noises and artifacts from becoming evident, allowing better image quality of composite image.

In the range where Threshold≦B_Intensity<B_th0, the transparent coefficient of the tissue velocity image is determined by line b. More specifically, the transparent coefficient a_Ib is determined by equation (2). This makes the tissue velocity image translucent, and B mode image can be seen therethrough. The composite image that gives such impression may be generated by weighted addition of the tissue velocity image on the B mode image. The weighted addition uses the following equation:

$$RGB\_Transparent = a\_Ib * RGB\_B + (1.0 - a\_Ib) * RGB\_Color$$

Where RGB_Transparent is data of three fundamental colors (R, G, B) indicative of the composite image. RGB_B is the data of three fundamental color indicative of monochrome B mode image. RGB_Color is the data of three fundamental colors indicative of the color tissue velocity image. Each data of three fundamental color is composed of 8 bits.

As shown in equation (3), the composite image is generated by adding the weight of B mode image as a_Ib, with the weight of tissue velocity image as 1−a_Ib. In the equation (3) above, the transparency coefficient a_Ib is used merely as the value indicative of the weight. Thus, the graph of transparent coefficient can be used as the graph of weights for weighted addition. The transparent coefficient a_Ib is called as weight hereinbelow.

It should be noted here that a_Ib taken as the weight of B mode image is reasonable, since when the transparency coefficient a_Ib is larger the transparency of tissue velocity image is increased so that the B mode image thereafter can be seen better. In addition, when the transparency of tissue velocity image increases the tissue velocity image may become less visible, so that 1−a_Ib taken as the weight of tissue velocity image is reasonable.

When B_th0≦B_Intensity, the weight is determined by line a. More specifically, the weight a_Ib can be given by equation (1). Then by substituting the weight of B mode image with a_Ib, and the weight of tissue velocity image with 1−613a_Ib, the pixel values of the composite image can be given by equation (3).

As can be seen from the foregoing, in the range of Threshold≦B_Intensity, a composite image of the B mode image well matched with the tissue velocity image can be given, by adding the weights of both B mode image and tissue velocity image in a complementary manner in relation to B_Intensity.

By appropriately using the equation of weight in response to the range to which the B_Intensity belongs so as to give the weight in relation to the polygonal linear function, the transparency adjustment optimal to each section to which B_Intensity belongs can be performed.

It can be conceivable that a multi-step polygonal linear function provides the weight by creating two or more setting point of crossing B_th0. This makes a finer transparency adjustment. Alternatively, the calculation of weight may be operated with a function of quadric or higher dimension, which yields a continuous curve.

In FIG. 4, there is shown a functional block diagram of the processor 148 for performing the formation of composite image as noted above. As can be seen in the figure, the processor 148 weights a_Ib and 1−a_Ib for the B mode image (B) and tissue velocity image (color) respectively, in the weighting units 152 and 154; forms a composite image (RGB_Transparent) by adding both images in the adder unit 156, then outputs through the black nullifying unit 158.

The weighting units 152 and 154 are an exemplary embodiment of the weight adjustment means in accordance with the present invention. The adder unit 156 is an exemplary embodiment of the adder means in accordance with the present invention. The black nullifying unit 158 is an exemplary embodiment of the black nullifying means in accordance with the present invention.

Many widely different embodiments of the invention may be configured without departing from the spirit and the scope of the present invention. It should be understood that the present invention is not limited to the specific embodiments described in the specification, except as defined in the appended claims.

The invention claimed is:

1. An ultrasonic image display method for displaying a composite image made from a B mode image and a tissue velocity image of an object taken by means of an ultrasonic imaging system, said method comprising:

receiving an echo receiver signal using a transceiver unit in response to ultrasound waves transmitted into the object by an ultrasonic probe, the echo receiver signal including a Doppler signal and a signal indicative of an intensity of echo at each reflection point on a sonic scan line;

processing a tissue velocity data component of the Doppler signal using a Doppler processing unit in order to generate the tissue velocity image;

decreasing a weight of the B mode image using a B mode processing unit while increasing a weight of the tissue velocity image in response to an increase of a brightness of the B mode image, the weight of the B mode image decreased based on a linear function when the brightness of the B mode image is less than a threshold and decreased based on at least one linear function when the brightness of the B mode image is greater than or equal to the threshold;

adding the weighted B mode image and the tissue velocity image using an image processing unit coupled to the Doppler processing unit and the B mode processing unit in order to form a composite image that is expressed by $$RGB\_Transparent = a\_Ib*RGB\_B + (1.0 - a\_Ib)*RGB\_Color;$$ and displaying the composite image using a composite image display unit coupled to the image processing unit.

2. An ultrasonic image display method according to claim 1, wherein the linear function is a polygonal line function.

3. An ultrasonic image display method according to claim 2, wherein the polygonal line function is made of a concatenation of a plurality of linear functions.

4. An ultrasonic image display method according to claim 3, wherein a joint of the plurality of linear functions is variable.

5. An ultrasonic image display method according to claim 3, wherein a slope of each linear function of the plurality of linear functions is variable.

6. An ultrasonic image display method according to claim 1, wherein in a black section where the brightness of the B mode image is less than the threshold, the B mode image and the tissue velocity image are nullified.

7. An ultrasonic image display method according to claim 6, wherein the threshold is variable.

8. An ultrasonic image display method according to claim 1, wherein processing a tissue velocity component of a Doppler signal comprises extracting the tissue velocity data component from a Doppler signal that includes the tissue velocity data component and a blood velocity data component.

9. An ultrasonic diagnosis apparatus for taking a B mode image and a tissue velocity image of an object by means of ultrasound to display a composite image of a weighted B mode image and the tissue velocity image, said ultrasonic diagnosis apparatus comprising:
a Doppler processing unit configured to process a tissue velocity data component of a Doppler signal and to generate the tissue velocity image based on the tissue velocity data component;
a weight adjustor device configured to decrease a weight of the B mode image in response to an increase of a brightness of the B mode image, while increasing a weight of the tissue velocity image, the weight of the B mode image decreased based on a linear function when the brightness of the B mode image is less than a threshold and decreased based on at least one linear function when the brightness of the B mode image is greater than or equal to the threshold;
an adder device configured to add the weighted B mode image and the tissue velocity image to obtain the composite image based on the equation $$RGB\_Transparent = a\_Ib*RGB\_B + (1.0 - a\_Ib)*RGB\_Color;$$ and a display device configured to display the composite image obtained from the addition.

10. An ultrasonic diagnosis apparatus according to claim 9, wherein the linear function is a polygonal linear function.

11. An ultrasonic diagnosis apparatus according to claim 10, wherein the polygonal linear function is made of a concatenation of a plurality of linear functions.

12. An ultrasonic diagnosis apparatus according to claim 11, wherein a joint of the plurality of liner functions is variable.

13. An ultrasonic diagnosis apparatus according to claim 11, wherein a slope of each linear function of the plurality of linear functions is variable.

14. An ultrasonic diagnosis apparatus according to claim 9, further comprising:
a black nullifying device configured to nullify the B mode image and the tissue velocity image for a black section in which the brightness of the B mode image is less than the threshold.

15. An ultrasonic diagnosis apparatus according to claim 14, wherein the threshold is variable.

16. An ultrasonic diagnosis apparatus according to claim 9, wherein said Doppler processing unit is configured to extract the tissue velocity data component from a Doppler signal that includes the tissue velocity data component and a blood velocity data component.

17. An ultrasonic diagnosis apparatus comprising:
an ultrasonic probe;
a transceiver coupled in signal communication to said ultrasonic probe, said transceiver configured to transmit driving signals to said ultrasonic probe to generate ultrasound waves and to receive echo signals from said ultrasonic probe, the echo signals generated in response to the driving signals;
a B mode processing unit coupled in signal communication to said transceiver, said B mode processing unit configured to generate a B mode image based on the echo signals received by said transceiver from said ultrasonic probe and transmitted by said transceiver to said B mode processing unit;
a Doppler processing unit coupled in signal communication to said transceiver, said Doppler processing unit configured to generate a tissue velocity image based on the echo signals received by said transceiver from said ultrasonic probe and transmitted by said transceiver to said Doppler processing unit, said Doppler processing unit further configured to generate the tissue velocity image by processing a tissue velocity data component of the received echo signals; and
an image processing unit coupled in signal communication to said B mode processing unit, said Doppler processing unit, and a display device, said image processing unit configured to:
decrease a weight of the B mode image in response to an increase of a brightness of the B mode image, while increasing a weight of the tissue velocity image, the weight of the B mode image decreased based on a linear function when the brightness of the B mode image is less than a threshold and decreased based on a plurality of linear functions when the brightness of the B mode image is greater than or equal to the threshold;
add a weighted B mode image and a weighted tissue velocity image using the equation $$RGB\_Transparent = a\_Ib*RGB\_B + (1.0 - a\_Ib)*RGB\_Color;$$ and transmit a composite image obtained from the addition to said display device.

18. An ultrasonic diagnosis apparatus according to claim 17, wherein the linear function is a polygonal linear function.

19. An ultrasonic diagnosis apparatus according to claim 18, wherein the polygonal linear function is made of a concatenation of a plurality of linear functions.

20. An ultrasonic diagnosis apparatus according to claim 19, wherein a joint of the plurality of liner functions is variable.

* * * * *

UNITED STATES PATENT AND TRADEMARK OFFICE
CERTIFICATE OF CORRECTION

PATENT NO.         : 7,608,044 B2                                           Page 1 of 1
APPLICATION NO.  : 11/200813
DATED              : October 27, 2009
INVENTOR(S)        : Shunichiro Tanigawa It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 385 days.

Signed and Sealed this

Twelfth Day of October, 2010

David J. Kappos
*Director of the United States Patent and Trademark Office*